United States Patent [19]

Muller

[11] Patent Number: 5,549,541
[45] Date of Patent: Aug. 27, 1996

[54] CONTINUOUS FLOW CYSTOSCOPE

[75] Inventor: Richard P. Muller, Bronx, N.Y.

[73] Assignee: Circon Corporation, Santa Barbara, Calif.

[21] Appl. No.: 344,559

[22] Filed: Nov. 23, 1994

Related U.S. Application Data

[63] Continuation of Ser. No. 17,475, Feb. 11, 1993, Pat. No. 5,392,765.
[51] Int. Cl.$^6$ ...................................................... A61M 3/00
[52] U.S. Cl. ............................................... 600/105; 604/43
[58] Field of Search ........................ 604/21, 43; 606/46; 600/15, 135, 153, 156

[56] References Cited

U.S. PATENT DOCUMENTS

| | | | |
|---|---|---|---|
| 2,076,741 | 4/1937 | Peck . | |
| 3,835,842 | 9/1974 | Iglesias . | |
| 3,850,175 | 11/1974 | Iglesias . | |
| 3,939,839 | 2/1976 | Curtiss | 600/105 X |
| 4,132,227 | 1/1979 | Ibe | 600/105 |
| 4,423,727 | 1/1984 | Widran et al. | 600/105 X |
| 5,031,603 | 7/1991 | Gautier et al. . | |
| 5,037,386 | 8/1991 | Marcus et al. | 604/43 |
| 5,095,889 | 3/1992 | Weissmuller et al. . | |
| 5,151,101 | 9/1992 | Grossi et al. | 606/46 |

OTHER PUBLICATIONS

*The Use of the Resectoscope in Gynecology*, by Richard A. Auhll, pp. 91 through 99, Oct. 11, 1990, Biomedical Business International.

*Primary Examiner*—John D. Yasko
*Attorney, Agent, or Firm*—Daniel J. Meaney, Jr.

[57] ABSTRACT

A continuous flow cystoscope is shown. The cystoscope includes an outer sheath having an outer surface, a hollowed out central area extending along a central axis which extends therethrough, a proximal section and a distal section. The distal section includes a distal end having a member defining an opening. In the preferred embodiment, the outer sheath opening is formed at an acute angle relative the central axis. The distal section of the outer sheath includes an elongated fenestra extending distally therefrom along a path substantially parallel to and spaced from the central axis. The proximal section of the outer sheath includes an inlet port and an outlet port. An inner member is positioned within the hollowed out central area of the outer sheath and includes an inner member channel having a first passageway which is adapted to receive a telescope and a second passageway which is utilized for passing a working tool, such as a laser fiber. The outer sheath and the inner member are spaced apart to form an outflow fluid passageway therebetween. The inner member includes a distal section which has an irrigation inlet and a distal end. The irrigation inlet and distal end are positioned in the opening of the distal section of the outer sheath. The inner member includes an elongated lip which cooperates with the elongated fenestra of the outer sheath to form a fenestra channel having an irrigation outlet. The fenestra channel communicates with the fluid passageway. The inner member channel communicates with the inlet port for passing fluid therethrough to irrigate an operative site. The fenestra channel passes fluid emanating from the irrigation inlet over a flow path having reduced fluid turbulence to the irrigation outlet, through the fenestra channel, through the fluid passageway and through the outlet port of the outer sheath.

12 Claims, 2 Drawing Sheets

5,549,541

CONTINUOUS FLOW CYSTOSCOPE

RELATED APPLICATION

This is a continuation of application Ser. No. 08/017,475 filed Feb. 11, 1993, which issued as U.S. Pat. No. 5,392,765 on Feb. 28, 1995.

BACKGROUND OF THE INVENTION

1. Field of the Invention

This invention relates to a continuous flow instrument, such as a continuous flow endoscope, which may be used as a hysteroscope or cystoscope and more particularly relates to a continuous flow cystoscope having an outer sheath which has a hollowed-out central area which terminates in a distal end having an elongated fenestra and a means for defining an inner member which is located within the hollowed-out central area wherein the means defining the inner member includes means for defining an inner member channel having a first passageway for receiving a telescope and a second passageway for passing a working tool. The inner member channel terminates in a distal end having an irrigation inlet. The inner member further includes means defining an elongated lip. The inner member is spaced from the inner surface of the outer sheath to define a fluid passageway for irrigant outflow and the elongated fenestra of the outer sheath and the elongated lip of the inner member cooperate to define a fenestra channel having an irrigation outlet. The fenestra channel communicates with the fluid passageway. In a procedure, irrigation fluid is passed to the operative site through the inner member channel and through the irrigation inlet. Irrigation fluid is removed from the operative site by the irrigation outlet, which passes the fluid through the fenestra channel into the fluid passageway to an outlet port at the proximal end of the outer sheath. The flow path traversed by the fluid is along a path having reduced fluid turbulence at the irrigation inlet and operative site. The second passageway may be used to pass a working tool such as a laser fiber for the incision, excision, ablation and hemostasis of the lower genitourinary tract including prostatic tissue.

2. Description of the Prior Art

Continuous flow resectoscopes are well known in the art. U.S. Pat. No. 3,835,842 discloses a continuous flow resectoscope for use in urology. Continuous flow resectoscopes have been used for other surgical procedures. An article entitled, *The Use of the Resectoscope in Gynecology*, by Richard A. Auhll, appeared at pages 91 through 99 in the Oct. 11, 1990 issue of the Biomedical Business International (the "Auhll Reference") describes the use of the CIRCON ACMI uterine resectoscope system for gynecological procedures. The Auhll Reference discloses that the use of a continuous flow electrical resectoscope system (CFR) includes a continuous flow irrigation system. Multiple concentric sheaths allow continuous and simultaneous inflow and outflow of non-conducting irrigating solutions to the operative site so that the surgeon has a clear view through the solution. It is known in the art that the means for passing fluid into the uterus in order to distend the same cannot have the fluid pressure exceed an intrauterine pressure of 90 mm of mercury. If the fluid pressure exceeds 90 mm of mercury, then the fluid is absorbed into the tissue of the uterus which is undesirable in performing an OB-GYN procedure.

In addition, the continuous flow irrigation system provides sufficient flow and pressure to distend and expand the uterus to enable the surgeon to perform the desired procedure. Such a system is referred to as a Uterine Resectoscope System. The Uterine Resectoscope System is used for three operative procedures: (i) Myoma resection; (ii) endometrial ablation; and (iii) cynical septa dissection.

The presently known continuous flow resectoscope and continuous flow hysteroscope systems generally pass an irrigating fluid through the center of an inner sheath and out of the distal end to irrigate the operative site. Fluid is removed from the operative site by passing the fluid through a passageway formed between the outer surface of an inner sheath and the inner surface of an outer sheath. Typically, fluid flow is obtained by positioning the source of fluid at a predetermined height in the operating room. For example, positioning a bag of saline fluid at approximately 1 meter above the operating table will produce 75 mm of mercury head pressure. At a height of 1.4 meter produces approximately 103 mm of mercury pressure at the outlet of the source. The pressure drop through the various tubing and through the resectoscope drops the pressure to a range of 60 mm of mercury to 90 mm of mercury at the distal end of the hysteroscope.

Continuous flow hysteroscopes are known in the art and comprise an outer sheath having an outer surface, an inner surface and a hollowed out central area extending along a central axis. The outer sheath has an outer surface, an inner surface and a hollowed out central area extending along a central axis. The outer sheath has a distal section which terminates in a distal end and means are located at the distal section for defining around the outer surface of the sheath a plurality of openings which extend between the outer surface of the sheath and the inner surface. The plurality of openings pass fluid exterior to the distal section therethrough and into the hollowed out central area. The continuous flow hysteroscope further includes means defining an inner member positioned within the outer sheath for defining a fluid passageway which is adapted to pass irrigation fluid passed from the operation site through the plurality of openings into the fluid passageway and out of an outlet port located at the proximal end of the outer sheath. The inner member includes means defining a first channel and second channel which are adapted to receive a telescope and a working tool, respectively. An additional accessory or working channel may also be provided. The first and/or second channel pass irrigation fluid from an inlet port, through the inner member and out of the distal end of the inner member to the operative site. The irrigation fluid is passed over the distal end of the telescope and traverses a flow path to the plurality of openings which are located in substantially the same section as the distal end of the telescope.

An example of such a continuous flow hysteroscope is CIRCON ACMI Catalog No. GY8-CFH, Continuous Flow Hysteroscope.

SUMMARY OF THE INVENTION

The present invention discloses a novel, unique and improved continuous flow instrument which is adapted for use as a continuous flow cystoscope. In the preferred embodiment, the cystoscope comprises an outer sheath having an outer surface, an inner surface and a hollowed-out central area extending along a central axis which extends therethrough. The sheath has a proximal section and a distal section. The distal section includes means defining an opening and an elongated fenestra extending distally from the distal section of the outer sheath. The elongated fenestra extends along a path substantially parallel to and spaced from the central axis.

The cystoscope further includes means defining an inner member adopted to be positioned within said hollowed-out area wherein the inner member defining means includes means for defining an outer wall located around the periphery of the inner member which is adapted to be spaced from the inner surface of the outer sheath for defining a fluid passageway. The means defining the inner member includes means defining an inner member channel having a first passageway which is adapted to receive a telescope and a second passageway which is adapted for passing a working tool. The distal end of the inner member has an elongated lip which cooperates with the elongated fenestra to form a fenestra channel having an irrigation outlet. The inner member channel is operatively connected to an inlet port located at the proximal section of the outer sheath for passing fluid through the inner member channel, through an irrigation inlet located at the distal end of the inner member. The fluid flow path is through the inner member channel, past the distal end of a telescope and the working tool extending distally from the channel over a flow path having reduced turbulence to the irrigation outlet, through the fenestra channel, through the fluid passageway and through the outlet port of the outer sheath.

In addition, a novel and unique method for performing a surgical procedure using the instrument of the present invention is shown. The method for performing a surgical procedure comprises the step of assembling a continuous flow instrument comprising an outer sheath having an outer surface, and inner surface and a hollowed-out central area wherein the outer sheath has a proximal section having an outlet port and an inlet port and a distal section having an opening and an elongated fenestra extending therefrom and means defining an inner member positioned within the hollowed-out central area and wherein the inner member includes means for defining an exterior surface located around the periphery of the inner member which is adapted to be spaced from the inner surface of the outer sheath for defining a fluid passageway, means defining a distal end and an irrigation inlet wherein the distal end and irrigation inlet are positioned in the opening of the outer sheath and an elongated lip wherein the elongated lip cooperates with the elongated fenestra to define a fenestra channel which communicates with the fluid passageway, a first passageway for receiving a telescope and a second passageway for passing a working tool; and inserting the continuous flow instrument into a cavity.

As described hereinbefore, the prior art continuous flow hysteroscope systems utilize an outer sheath, an inner sheath, a visual obturator for introduction and diagnostic purposes, an operating bridge for operating procedures and additional components in order to perform diagnostic and/or operative procedures. As such, the prior art continuous flow resectoscope/hysteroscope systems having an inner sheath and outer sheath structure do provide a clear visualization of the uterine cavity during diagnostic and operative procedures. However, due to the outer sheath and inner sheath structure, the overall diameter of the outer sheath remained in the 10 mm to 12 mm range.

The prior art continuous flow hysteroscope eliminated the inner sheath and replaced the inner sheath with an inner member. As such, the same fluid throughput flow and the size of the accessory or working channel were maintained while reducing the overall outer sheath size or diameter. In the preferred embodiment, the outside diameter of the outer sheath is in the range of about 7 mm to about 8 mm. A smaller sheath size is important to enable the gynecologist to minimize dilation of the cervix prior to insertion of the hysteroscope into the uterine cavity. However, one of the operating problems associated with the continuous flow hysteroscope is that the path of fluid flow produces fluid turbulence in the vicinity of the distal end of the telescope which may, from time-to-time, partially or completely momentarily block the field of view or result in short durations of an obstructed outflow channel over the fluid flow path from the irrigation outlet at the distal end of the inner member to the plurality of holes in the distal section of the outer sheath. At other times in the procedure, the holes in the distal section of the outer sheath can be covered by tissue thereby preventing an outflow of irrigant. This obstruction of outflow is a particular problem in the urological continuous flow resectoscope because the outflow holes in the outer sheath are often covered by the urethral lining.

The continuous flow cystoscope of the present invention overcomes certain of the disadvantages of the prior art continuous flow instruments. In the continuous flow cystoscope of the present invention, the advantageous structural relationship between the outer sheath and inner member is maintained to take advantage of the reduced overall outer sheath size having a diameter, in the preferred embodiment, of about 8 mm. The reduced diameter of the overall sheath size is desirable to reduce trauma to a patient during insertion of the cystoscope into the urethra of a patient.

Further, another advantage of the present invention is that the outer sheath has an elongated fenestra formed on the distal section which cooperates with an elongated lip formed on the distal end of the inner member to define a fenestra channel. The fenestra channel has an irrigation outlet which is located distally from the irrigation inlet in the inner member and from a working tool which is passed through the inner member channel and positioned to extend beyond the distal end of the telescope viewing means positioned within the inner member. The distal tip of a telescope is located in the vicinity of the distal end of the inner member. As such, the irrigation fluid passes through the inner member channel and flows in a flow pattern past the distal end of the telescope and the distal end of the working tool. The structure and placement of the fenestra channel and the irrigation outlet for the fenestra channel result in the establishment of a flow of the irrigation fluid emanating from the distal end of the inner member over a flow path having reduced fluid turbulence in that the irrigation fluid converges at the irrigation outlet of the fenestra channel at a location distally remote from the irrigation inlet, the working tool and the distal end of the telescope. As such, the fluid flow has less turbulence and results in immediate removal of image impeding material such as blood or tissue in the fluid flow which would otherwise obstruct the field of view. Concurrently, the fluid flow path is in a direction which transports any image impeding material into the irrigation outlet, through the fenestra channel, through the fluid passageway and out of the outlet port located at the proximal end of the outer sheath.

Another advantage of the present invention is that the continuous flow cystoscope includes a shaped fenestra which is designed to provide visual atraumatic instrument introduction.

Another advantage of the present invention is that the continuous flow cystoscope consists of two basic components, an outer sheath and an inner member. In the preferred embodiment, the continuous flow cystoscope performs four basic functions which include: (i) providing an inner member in the form of an operating bridge with a first passageway which is adapted to receive a telescope; (ii) providing an inner member in the form of an operating bridge having a second passageway which can be used as an accessory or working channel; and (iii) providing an inflow which passes through the inner member and irrigation inlet to the operative site; and (iv) establishing a fluid flow path having reduced fluid turbulence in the vicinity of the distal end of the telescope and working tool.

Another advantage of the present invention is that the inner member provides a surgeon with a passageway for performing therapeutic procedures such as, for example, for the incision, excision, ablation and hemostasis of the lower genitourinary tract including prostatic tissue. If the surgeon desires to perform an operative procedure requiring the use of a laser fiber, the inner member channel is sized to permit easy insertion and transporting of the laser fiber into and through a second passageway defined by the inner member channel. When the distal tip of the laser fiber extends distally from the inner member channel, the laser tip can be positioned in the desired location at the operative site in the cavity, all under the view of the telescope located in the first passageway defined by the inner member channel. The established flow pattern maintains an unobstructed field of view, facilitating consistent, clean, visualization of the operative site.

Another advantage of the present invention is that the inflow of irrigation fluid into the operative site is provided by means of the inner member channel which provides a passageway for the working tool. If the working tool is a laser fiber, the irrigation fluid concurrently provides a cooling medium for the laser tip. Fluid is removed from the operative site by the fenestra channel located at the distal end of the outer sheath directing the fluid away from the field of view at the irrigation outlet. The fluid passes from the fenestra channel through the fluid passageway formed between the outer wall of the inner member and the inner wall of the outer sheath. The fluid is then passed from the fluid passageway through an outlet port located at the proximal end of the outer sheath.

Another advantage of the present invention is that the unique sheath configuration maximizes irrigation fluid flow during laser procedures which is highly desirable when performing laser procedures in the urinary tract.

Another advantage of the present invention is that the elongated fenestra located at the distal end of the outer sheath is used to protect the non-lasing surface of a side firing or lateral firing laser fiber from coming into direct contact with tissue.

Another advantage of the present invention is that the continuous flow cystoscope comprising the outer sheath and means defining the inner member can be used in a cystoscopy procedure. The method includes the steps of assembling the outer sheath with a means for defining an inner member to form the continuous flow cystoscope. The means for defining the inner member comprises an inner member channel having a first passageway for receiving a telescope, and a second passageway for passing a working tool which, in the preferred embodiment, is a side firing laser fiber.

Another advantage of the present invention is that the method for performing a cystoscopy procedure can include the step of applying an irrigation fluid under selected pressure to an inlet port for forming inward fluid flow which is directed through the inner member channel out of the irrigation inlet of the inner member and applying a negative pressure to the outlet port to urge irrigation fluid external to the distal section through the irrigation outlet, fenestra channel, through the fluid passageway and through the outlet port to form a continuous fluid flow at the operative site which is directed away from the telescope viewing means.

Another advantage of the present invention is that the continuous flow instrument of the present invention could be used for other procedures such as a hysteroscopic procedure or the like.

BRIEF DESCRIPTION OF THE DRAWINGS

These and other advantages of the invention will be readily apparent when considered in light of the detailed description hereinafter of the preferred embodiment and of the drawings which include the following figures.

DESCRIPTION OF THE PREFERRED EMBODIMENT

Figure 1:
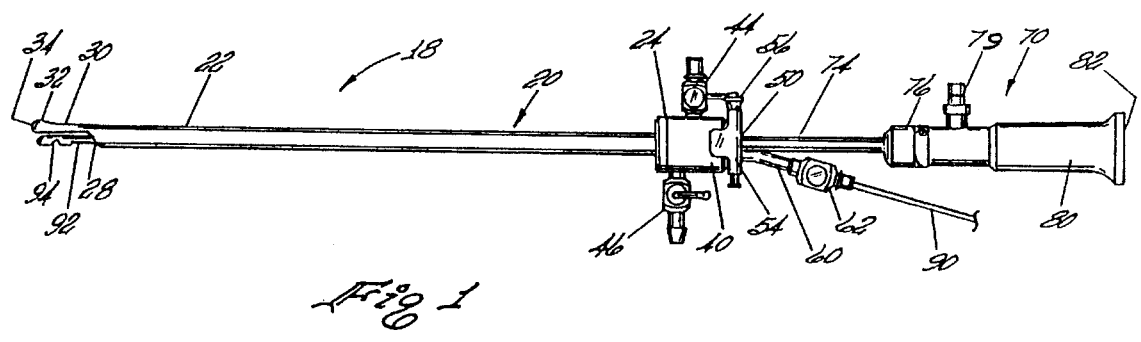
FIG. 1 is a front elevational view showing the continuous flow cystoscope which is fully assembled and which has a telescope located in the inner member first passageway and which has a side firing laser inserted into the inner member second passageway.

FIG. 1 illustrates an instrument generally as 18, which, in the preferred embodiment is a continuous flow cystoscope. The continuous flow cystoscope 18 is adapted to be utilized for performing therapeutic procedures in the urinary tract, and in particular, in the prostatic urethra and bladder cavity.

The terminology used herein to define fluid flow is based on the criteria that any orifice, channel, port or opening through which fluid enters the operative site or cavity is referred to by the term "inlet" and any such orifice, channel, port or opening through which fluid leaves the operative site or cavity is referred to by the term "outlet."

As illustrated in FIG. 1, the instrument 18 includes a means 20 for defining an outer sheath 22 having a distal section 30 and means for defining an opening 28. The distal section 30 of the outer sheath 22 includes a means for defining an elongated fenestra 32 which extends along a predetermined path relative to the distal section 30. The outer sheath 22 has an elongated central axis and the elongated fenestra 30 extends along a predetermined path which is substantially parallel relative to the central axis.

The outer sheath 22 further includes a proximal end 24 which includes a first connecting means 40, which has an inlet port 44 and an outlet port 46. FIG. 1 further depicts that the continuous flow cystoscope 18 includes a means 50 defining an inner member 58 (see FIG. 2b) having an inner member channel 78 (see FIG. 2b), which is positioned within the means defining the outer sheath 20. The means 50 defining the inner member 58 (see FIG. 2b), when positioned within the outer sheath 22, forms a fluid passageway therebetween. The inner member defining means 50 includes means for defining a telescope guide tube 74, which has an opening 76 at one end thereof which is adapted to receive a telescope shown generally as 70. The telescope guide tube 74 is operatively connected to a second connecting means 54 and communicates with the inner member channel 78 which is an open, oblong shaped channel. The inner member channel 78 defines a passageway which is adapted to receive a telescope to pass a working tool. The telescope includes a light post 79 which is adapted to have a light carrier affixed thereto and includes an eyepiece 80 with an opening 82 to enable the cystoscope to be viewed directly by a surgeon or to have a video camera affixed thereto.

As illustrated in FIG. 1, the means 50 defining the inner member 78 includes a working tool guide tube 60 includes an opening 62 which is adapted to pass a working tool such as a laser fiber at 90. The laser fiber at 90 is passed through the working tool guide tool 60 into the inner member channel 78 and is advanced sufficiently through the inner member channel 78 such that the distal end of the laser 92 having a lasing surface 94 is passed distally through the opening 28 and positioned relative to the distal end of the telescope 80. The surgeon can view the position of the laser tip 94 through the distal end of the telescope 28. As illustrated in FIG. 1, the elongated fenestra 32 is positioned to protect the non-lasing surface of the laser tip 94 to prevent the same from contacting other tissue.

Figure 2A:
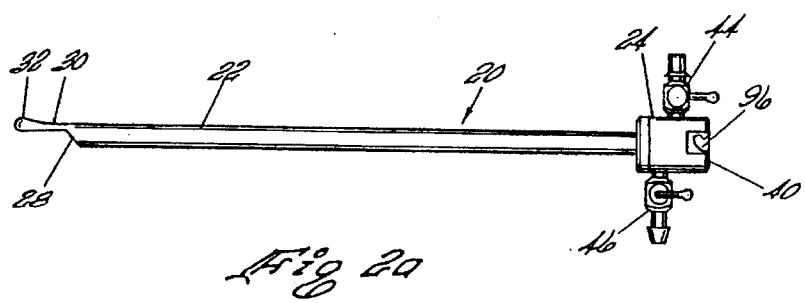
FIG. 2a is a front elevational view of the outer sheath showing the elongated fenestra located at the distal end of the outer sheath, the inlet port, the outlet port and the first connecting means located at the proximal end of the outer sheath.
Figure 2B:
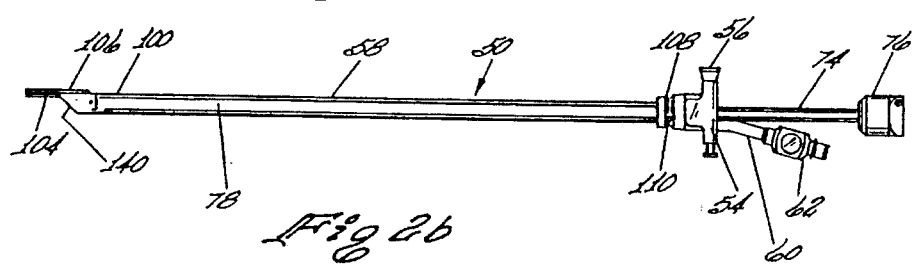
FIG. 2b is a front elevational view of the means defining the inner member showing the inner member having a second connecting means, means defining the first passageway, means defining the second passageway and means defining the irrigation inlet and the elongated lip located at the distal end of the inner member.

The long fenestra 32 cooperates with an elongated lip, shown as elongated lip 104 in FIG. 2b, of the means 50 defining an inner member 58 to form a fenestra channel. The fenestra channel 36 which includes an irrigation inlet shown as 34 in FIG. 1.

FIG. 2a shows the details of the outer sheath 22. As illustrated in FIG. 2a, the distal section 30 terminates in an elongated fenestra 32 having a shaped tip in the form of a raised smooth member. The shape of the tip is illustrated in greater detail in FIG. 4. The shape tip of the fenestra is selected so as to reduce trauma when the distal end of the cystoscope is inserted into the urethra and advanced to position the distal end of the cystoscope at a predetermined location within the urethra. Since the preferred embodiment of the continuous flow cystoscope is for performing a for the incision, excision, ablation and hemostasis of the lower genitourinary tract including prostatic tissue, the distal end of the continuous flow cystoscope would be advanced within the urethra of a male until the distal end thereof is positioned relative to the prostate where the for the incision, excision, ablation and hemostasis of the lower genitourinary tract including prostatic tissue procedure is to be performed.

In FIG. 2a, the outer sheath 22 is shown to include the first connecting means 40 which includes an inlet port 44 and the outlet port 46. The first connecting means 40 includes an insertion member 96 which is adapted to releasably connect to the second connecting means 54 located on the means 50 defining the inner member 58 as illustrated in FIG. 2b. FIG. 2a also illustrates that opening 28 is formed at an acute angle relative to the central axis. This may be referred to as a slanted opening. The opening has an oblong shape as illustrated by opening 28 in FIG. 3.

FIG. 2b illustrates in greater detail the structure of the means defining the inner member 58. The means 50 defining the inner member 58 includes a distal section 100. The distal section 100 includes means for defining an irrigation inlet 140 and an elongated lip 104 which has a protrusion section 106 formed therein which is substantially triangular in shape. The irrigation inlet 140 is slanted in the same manner as that of the opening 28. In the preferred embodiment, the opening 28 and irrigation inlet 140 are substantially coplaner.

Figure 4:
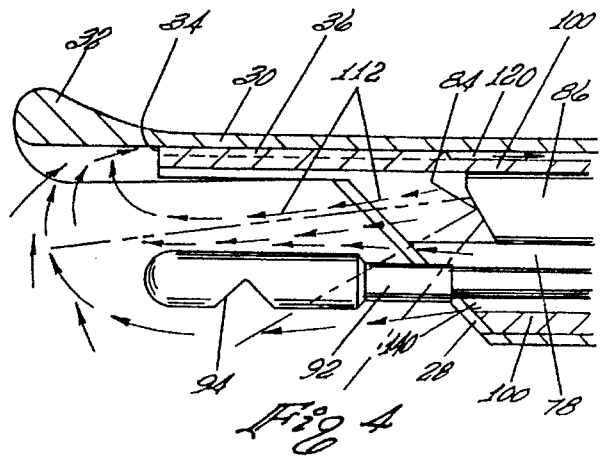
FIG. 4 is a partial cross sectional view of the distal end of the continuous flow cystoscope showing the fluid flow from the irrigation inlet of the inner member past the distal end of the telescope and the working tool and into the irrigating outlet of the fenestra channel.

The elongated lip 104 having the protrusion 106 which cooperates with the elongated fenestra 32 of the outer sheath 22 to form the irrigation outlet 34 and the fenestra channel 36. The fenestra channel 36 is illustrated in FIG. 4. The fenestra channel 36 and irrigation outlet 34 are located at the distal end of the fenestra 32 and elongated lip 104 location.

FIG. 2b also illustrates that the proximal end of the inner member 58 includes a second connecting means shown generally as 54 which cooperates with a spring loaded latch 56 to removeably connect the second connecting means 54 to the first connecting means 40 of the outer sheath 22. The second connecting means 54 includes a raised boss having a groove 108 which defines an inlet channel which cooperates with one or more inlet openings 110 which are adapted to cooperate with the inlet port 44 located in FIG. 2a. Irrigation fluid will flow through the inlet port 44 to the inlet opening 110 which passes the fluid into the inner member channel 78. The outlet port 46 is operatively coupled through an outlet channel internal to the first connecting means 24 to the fluid passageway defined being the outer sheath 20 and inner member 50.

FIG. 2b illustrates that the telescope guide tube 74 terminates in a housing 76 which is adapted to receive and support the telescope 70 as illustrated in FIG. 1. The working tool guide tube 60 includes an opening 62 which is adapted to pass a working tool, such as, for example, a side firing laser fiber. Each of the telescope guide tube 74 and the working tool guide tube 60 terminates in the second connecting means 54 and the ends thereof communicate with the inner member channel 78. The telescope guide tube 74 cooperates with the first passageway of the inner member channel 78 to pass the telescope 80. Similarly, the working tool guide tube 60 cooperates with the second passageway of the inner member channel 78 to pass the working tool 90.

Figure 3:
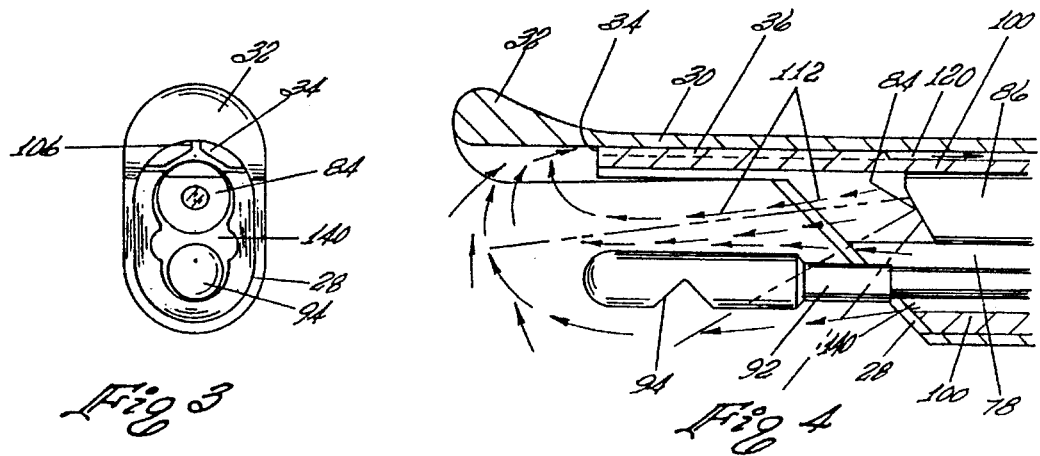
FIG. 3 is a left end elevational view of the distal end of the continuous flow cystoscope showing the telescope distal end, the laser fiber, irrigation inlet and irrigation outlet.

FIG. 3 illustrates in detail the structural arrangement of the assembled continuous flow cystoscope. The outer sheath 22 terminates in the fenestra 32 and defines an opening 28. The distal end opening of the inner member 58 defines the irrigation inlet 140. The means 50 defining the inner member 58 includes means for defining the inner member channel 78 having on the upper section thereof the first passageway which is adapted to receive the telescope 80 having distal end 86 having on the lower section thereof a second passageway which is adapted to receive the laser fiber 92. As illustrated in FIG. 3, the irrigation inlet 140 and the distal end of the inner member 58 are located within the opening 28 of the outer sheath 22.

The distal end 100 of the inner member 58 terminates in the elongated lip 104 having the protrusion 106 formed thereon. The elongated lip 104 cooperates with the elongated fenestra 32 to define the irrigation outlet 34 and the fenestra channel 36.

FIG. 4 illustrates in greater detail the structural and operative relationship between the outer sheath 22 and the inner member 58. The outer sheath 22 has its distal end 30 illustrated in the form of an elongated fenestra 32 having a shaped tip at the end thereof to facilitate atraumatic insertion of the distal end of the cystoscope into the urethra. The outer sheath 22 includes means for defining an opening 28. The opening 28 is sized to receive the distal end 100 of the inner member 58 including the irrigation inlet 140.

FIG. 4 illustrates that the distal end of the telescope 86 has a viewing lens 84 positioned in the vicinity of the irrigation inlet 140 in the distal end 100. The working tool, which in the preferred embodiment is a side firing laser fiber, has a distal laser fiber end 92 which terminates in a lasing surface 94. The non-lasing surface is spaced from and protected by the elongated fenestra 32.

FIG. 4 illustrates by means of arrows 112 the fluid flow of irrigation fluid. The irrigation fluid passes through the inner member channel 78 including the first passageway and second passageway and passes out the irrigation inlet 140. As illustrated in FIG. 4, the fluid flow maintains a relatively linear direction of movement as it passes from the irrigation inlet 140 past the distal end 86 of the telescope 70 including the lens surface 84 thereof, past the laser fiber distal section 92 including the lasing surface 94 to the distal end of the elongated fenestra 32 where the fluid is then drawn into the irrigation outlet 34 and into the fenestra channel 36 and through the fluid passageway 120.

The fluid flow path is such that there is reduced turbulence in the vicinity of the telescope lens 84 in that image impeding materials, such as blood or tissue, are immediately removed by the linear flow of irrigation fluid away from the viewing means 84 and towards the fenestra channel 36 for removal.

Thus, a fluid flow is established which has reduced fluid turbulence, which improves the field of view and which transports image impeding material promptly and immediately from the operative site.

Figure 5:
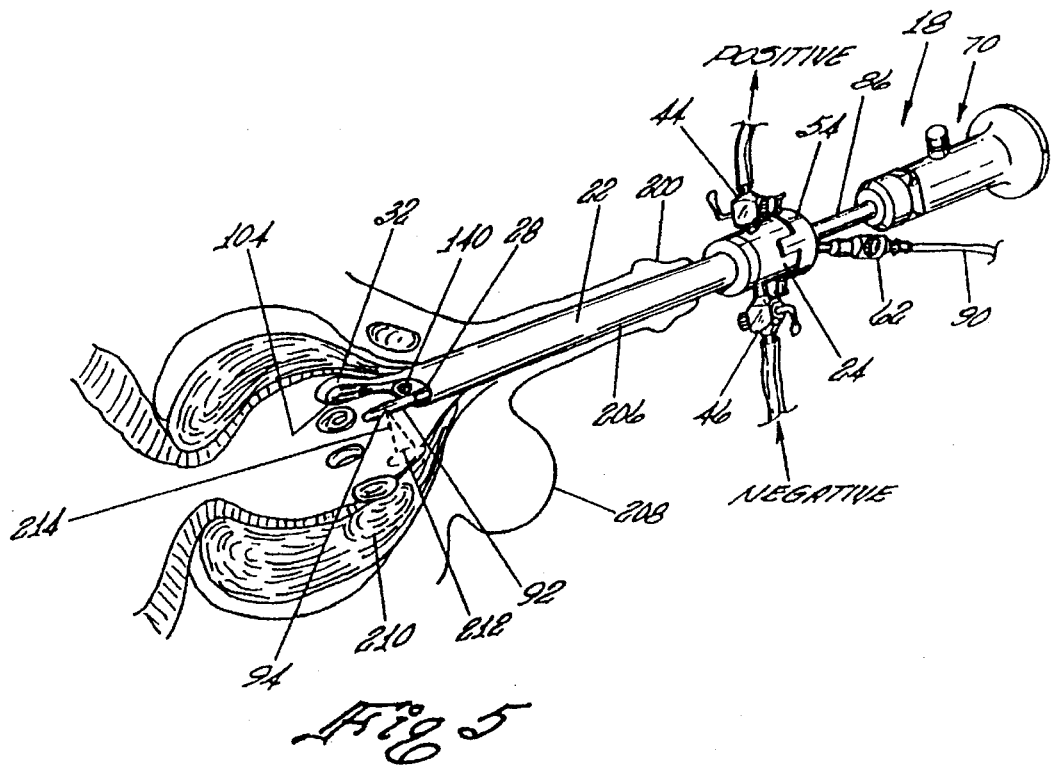
FIG. 5 is a pictorial representation of the continuous flow cystoscope performing an incision, excision, ablation and hemostasis of the lower genitourinary tract including prostatic tissue procedure.

FIG. 5 illustrates a method for performing a procedure utilizing the continuous flow cystoscope of the present invention. As illustrated in FIG. 5, the continuous flow cystoscope 18 has been inserted through the urethra 206 of the penis 200 of a male into the area of the prostate shown generally as 210 which is located beyond the testicles 208. The proximal end 24 of the outer sheath 22 has the inlet port 44 operatively connected to a source of irrigation fluid under positive pressure. The outlet port 46 is illustrated as being operatively connected to a negative pressure. A laser fiber 90 is shown in position in the working tool guide tube 60 and the distal end 92 of the laser fiber 90 having the lasing surface 94 is likewise illustrated. The outer sheath 22 is passed through the urethra 206 of the penis 200 and past the testicles 208 into the area of the prostate illustrated as 210. The elongated fenestra 32 is shown supporting the opposite side of the prostate in a position to enable the urologist to specifically identify an operative site in the prostate 210 for the incision, excision, ablation and hemostasis of the lower genitourinary tract including prostatic tissue. When the appropriate operative site has been located and the desired fluid flow has been determined, the laser fiber 90 is actuated to produce the laser radiation shown generally as 214 to necrosis the tissue.

Figure 6:
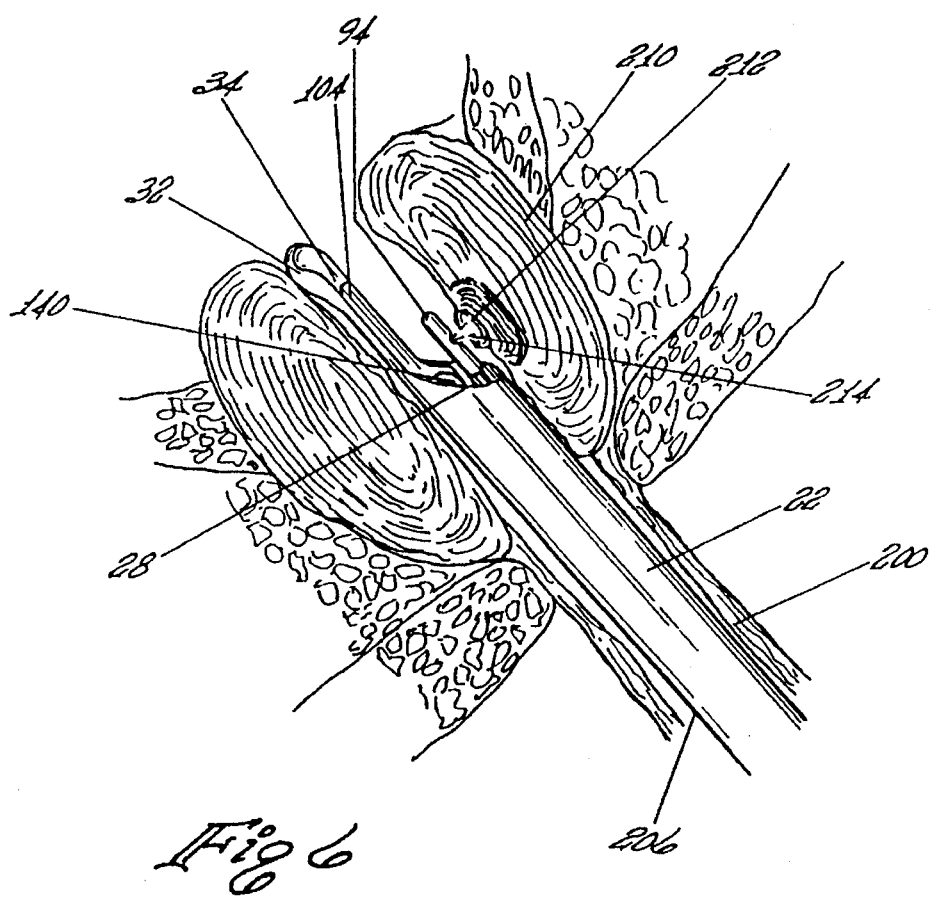
FIG. 6 is another pictorial representation showing the relationship between the elongated fenestra and the side firing laser.

FIG. 6 illustrates in a pictorial representation the distal tip structure wherein the opening 28 of the outer sheath 22 encloses the distal section 100 of the inner member 58 and the irrigation opening 140. The elongated lip 104 cooperates with the elongated fenestra 32 to define the irrigation outlet 34 and fenestra channel 36 to establish the generally linear fluid flow as illustrated in FIG. 4. FIGS. 5 and 6 illustrate a method for performing a medical procedure comprising the steps of assembling an instrument 20 comprising means defining an outer sheath 22 having an outer surface and a hollowed out central area where the outer sheath 22 has a proximal section 24 and a distal section 30 wherein the distal section 30 includes means for defining an opening 28 which communicates with the hollowed out central area and means for defining an elongated fenestra 32 and means 50 defining an inner member 58 positioned within the hollowed out central area of the outer sheath 22 and the means 50 defining the inner member 58 includes means for defining a distal end 100 and means for defining an irrigation inlet 140 wherein the distal end 100 and the irrigation inlet 140 are positioned within the opening 28 and the elongated lip 104 wherein the inner member forms a fluid passageway 120 which communicates with the fenestra channel 34 formed between the outer sheath 22 and the inner member 58 and wherein the elongated fenestra 30 of the outer sheath 22 and the elongated lip 104 of the inner member 58 defines a irrigation outlet 34 and a fenestra channel 36 which communicates with the fluid passageway 120, an inner member channel 78 for receiving a telescope 80 and a working tool such as a laser fiber 90.

FIGS. 5 and 6 would then require the step of applying an irrigating fluid, as illustrated in FIG. 4, to an inlet port 44 located at the proximal section of the outer sheath 22 which is operatively coupled to the inner member channel 78 for passing the irrigation fluid therethrough and out the irrigation inlet 140.

As illustrated in FIG. 4, during the application of fluid flow, the step of applying an irrigation fluid to the inlet and passing irrigation fluid shown by arrows 110 through the inner member channel 78 and around the side firing laser fiber 94 cools the laser fiber and concurrently irrigates the operative site.

As discussed hereinbefore, the preferred embodiment of the present invention is as a continuous flow laser cystoscope. The continuous flow laser cystoscope can be utilized for performing both diagnostic and therapeutic procedures in the urinary tract. One application for the present application is in the incision, excision, ablation and hemostasis of the lower genitourinary tract including prostatic tissue for male patients. The urologist can utilize the continuous flow cystoscope together with a side firing laser to visually and precisely control necrosis of the prostate tissue and to insure that the laser tip is properly cooled during the procedure. The fluid flow path is such that image impeding material in the form of tissue or blood which would otherwise impede visualization of the surgeon is continually removed in a direction away from the viewing means, thereby reducing fluid turbulence and thereby providing an unobstructed flow of irrigation fluid across the irrigation site.

The same principles; can be utilized in a continuous flow resectoscope for performing other surgical procedures or can be utilized as a continuous flow hysteroscope for performing gynecological procedures.

It is envisioned that the fluid flow in a continuous flow hysteroscope could be precisely controlled to insure that a predetermined pressure limit is not exceeded.

The irrigation flow through the continuous flow instrument could be controlled by gravity such as from a bag of saline fluid supported from an I.V. stand or positive fluid flow could be effected by an input pump or output pump or both which could be precisely controlled.

What is claimed is:

1. An instrument comprising means defining an outer sheath having a distal section wherein said distal section includes means for defining an opening and means defining an elongated fenestra having an under surface which extends along a predetermined path relative to said distal section; and means defining an inner member positioned within said means defining said outer sheath for forming a fluid passageway therebetween, said inner member defining means including a distal tip having an irrigation inlet and wherein said distal tip and irrigation inlet are positioned within said opening, said inner member defining means further including means defining at said distal tip an elongated lip having a length which is less than that of the fenestra, enabling the under surface of the fenestra to extend beyond the elongated lip, said elongated lip having a protrusion section which is substantially triangular in shape;

said fenestra defined by said means defining said outer sheath cooperating with said elongated lip and said protrusion section defined by said means defining said inner member for forming a fenestra channel having an irrigation outlet defined by said protrusion section spaced remotely from said irrigation inlet wherein the under surface of the elongated fenestra extends beyond the irrigation outlet to capture and direct the fluid to the irrigation inlet enabling said fenestra channel to pass fluid emanating from the irrigation inlet over a flow path minimizing fluid turbulence at the irrigation inlet to the under surface of the fenestra, to the irrigation outlet through the fenestra channel and to the fluid passageway.

2. The instrument of claim 1 wherein said elongated lip includes a protrusion extending in a direction towards the elongated fenestra.

3. The instrument of claim 2 wherein said elongated fenestra is shaped into a raised smooth member to facilitate atraumatic insertion of the instrument into a urethra.

4. The instrument of claim 1 wherein said inner member defining means includes means for defining a first passageway for receiving a telescope; and a second passageway for passing a working tool.

5. The instrument of claim 1 wherein said opening and irrigation inlet are formed at an acute angle relative to the central axis.

6. The instrument of claim 5 wherein the outer sheath opening and the irrigation inlet are oblong shaped.

7. The instrument of claim 1 wherein said outer sheath opening and irrigation inlet are substantially coplanar.

8. The instrument of claim 1 wherein said inner member defining means including means for defining an inlet which is operatively coupled to a means defining an inner member channel which defines said first passageway and said second passageway.

9. The instrument of claim 8 wherein said inner member defining means further includes means for defining an inlet which is operatively coupled to each of said first passageway and said second passageway.

10. The instrument of claim 9 wherein said outer sheath includes a first connecting means located at the proximal section of said outer sheath, said first connecting means including means defining an inlet channel which communicates with an inlet port for passing fluid from the first connecting means through the inner member to the irrigation inlet; and means defining an outlet channel which communicates with an outlet port for passing fluid form said fluid passageway to the outlet port.

11. The instrument of claim 1 wherein said elongated fenestra is formed with a raised smooth protrusion to reduce trauma during insertion of the instrument into a cavity during a procedure.

12. The instrument of claim 10 wherein said means defining said inner member further includes a second connecting means which is removeably connected to said first connecting means of said outer sheath for coupling said outer sheath to said inner member when said inner member is positioned within the hollowed-out central area of said sheath.

* * * * *